(12) United States Patent
Anderegg (10) Patent No.: US 9,717,629 B2
(45) Date of Patent: Aug. 1, 2017

(54) LASER SCANNER APPARATUS AND METHOD

(71) Applicant: LUMENIS LTD., Yokneam Ilit (IL)

(72) Inventor: Jesse Peter Anderegg, Layton, UT (US)

(73) Assignee: LUMENIS LTD, Yokneam (IL)

( * ) Notice: Subject to any disclaimer, the term of this patent is extended or adjusted under 35 U.S.C. 154(b) by 338 days.

(21) Appl. No.: 14/530,897

(22) Filed: Nov. 3, 2014

(65) Prior Publication Data

US 2015/0133899 A1    May 14, 2015

Related U.S. Application Data

(60) Provisional application No. 61/901,675, filed on Nov. 8, 2013.

(51) Int. Cl.
*A61F 9/008*    (2006.01)
*G02B 26/10*    (2006.01)

(52) U.S. Cl.
CPC ........ *A61F 9/00823* (2013.01); *G02B 26/105* (2013.01); *A61F 2009/00897* (2013.01)

(58) Field of Classification Search
CPC ....... A61F 2009/00897; A61F 9/00823; G02B 26/105
See application file for complete search history.

(56) References Cited

U.S. PATENT DOCUMENTS

| 6,033,396 | A | 3/2000 | Huang et al. | |
| 2004/0186462 | A1* | 9/2004 | Murakami | A61F 9/008 606/4 |
| 2007/0121069 | A1* | 5/2007 | Andersen | A61B 3/0008 351/221 |
| 2009/0051991 | A1 | 2/2009 | Kuribayashi | |
| 2011/0028948 | A1* | 2/2011 | Raksi | A61F 9/008 606/4 |
| 2011/0245816 | A1 | 10/2011 | Abe | |
| 2011/0306919 | A1* | 12/2011 | Latina | A61N 5/0613 604/20 |
| 2011/0319874 | A1 | 12/2011 | Mintz et al. | |
| 2012/0184857 | A1 | 7/2012 | Yokosuka | |

* cited by examiner

*Primary Examiner* — Gary Jackson
*Assistant Examiner* — Scott T Luan
(74) *Attorney, Agent, or Firm* — Isus Intellectual Property PLL (57) ABSTRACT

An apparatus for ophthalmic procedures contains a source of aiming and treatment laser beams, folded mirrors and lens arrays to cause the formation of a static pupil on a delivery mirror for observation and treatment by an operator of the apparatus.

26 Claims, 7 Drawing Sheets

VIEW A-A

FIG. 7

LASER SCANNER APPARATUS AND METHOD

RELATED APPLICATIONS

This application claims priority to U.S. Provisional Application No. 61/901,675, filed Nov. 8, 2013, the entirety of which application is herein incorporated by reference.

FIELD OF THE INVENTION

This invention relates generally to medical lasers, and relates more particularly to a laser device for scanning and treating target tissue for use linked to a binocular observation device for observing an area of the target tissue during scanning and treatment, to a system for scanning and treating target tissue comprising such a laser device linked to such a binocular observation device, to a method of scanning a laser beam onto a target tissue by projecting the laser beam through such a binocular observation device, and to a method of surgical or aesthetic treatment using such a system for scanning and treating target tissue, in particular in areas to which access is hampered or confined, such as in ophthalmic retinal procedures.

When used herein the term 'aiming beam' means a laser beam in a laser device for scanning and treating target tissue, which may be scanned to draw the treatment pattern on the target tissue and to draw on a different location information such as the working parameters of the laser. When the device is used linked to a binocular observation device, the latter allows changing of the parameters without the necessity for the operator to raise his/her head from the binoculars. In for example ophthalmic retinal surgical laser treatment, the aiming beam may also be used to fixate the patient's eye. For these purposes, the aiming beam is visible.

The aiming beam generally has a lower energy density than the treatment beam in the device (see below), and may often move faster than treatment beam in scanning.

When used herein the term 'treatment beam' means a laser beam in a laser device for scanning and treating target tissue, which may be scanned to follow a treatment pattern on the target tissue, for example drawn on various locations on the target tissue by an aiming beam. The treatment beam may be visible or not.

When used herein the term 'delivery mirror' means a planar mirror in a laser device for scanning and treating target tissue, the mirror being for projecting a laser beam, ordinarily from an aiming or treatment laser source, onto target tissue, the beam incident on the target tissue typically comprising treatment spots, on the target tissue of desired dimensions and layout.

When the laser device is used linked to a binocular observation device, the mirror is located between the longitudinal axes of the two components of the binoculars, and deflects the aiming and treatment beams to be coincident with the central optical axis of a binocular observation device, often in a direction orthogonal to their direction upstream of the mirror, and onto the area of target tissue to be treated.

When used herein the term 'scanning mirror' means one of a pair of mirrors which is located in the aiming or treatment beam path of a laser device for scanning and treating target tissue, each mirror being close to the other and independently rotatable about mutually orthogonal axes which are also orthogonal to the laser beam incident on the mirrors. The mirrors are commonly attached to galvanometers, which are powered up to cause the mirrors to rotate to generate a desired two dimensional pattern in the output beam. The two mirrors are separated by a small clearance which allows the two mirrors to move independently without fouling each other, and preferably avoids optical interference between them.

The laser beam is then projected via an array of field lenses and a delivery mirror, onto the target tissue, in a pattern, typically of treatment spots, of desired dimensions and layout, for example moving the laser beam across a treatment area until the area has been covered homogenously or so as to create an array of discrete spots, which may be in a variety of sizes, densities and patterns.

It is known in the surgical laser treatment industry to use the type of system for scanning and treating target tissue referred to above, in particular in areas to which access is hampered or confined, such as in ophthalmic retinal procedures.

As noted above in the definition of the delivery mirror, the mirror in such a system creates a scanned laser beam coincident with the central optical axis of a binocular observation device.

The delivery mirror is often located between the longitudinal axes of the two components of the binoculars, and frequently in a limited space. It is desirable that the mirror does not encroach on the binocular field of view in the observation device, and this element preferably needs to be invisible. In contrast, it is desirable that the area of target tissue scanned by a laser beam from the limited area of the delivering mirror is relatively large, preferably as large as possible.

However, in such systems known in the industry, scanning of the target tissue is generally effected by scanning the aiming and treatment laser beams across the delivery mirror. This design imposes restrictions on the size of the observed area of target that can be scanned by a laser beam from the limited area of the delivering mirror. Indeed, there is a directly proportionate linkage between the size of the scanned treatment area and the size of the delivery mirror. In order to increase the treatment area a bigger delivery mirror is required. Additionally, the delivery mirror needs to be relatively large, certainly larger than in corresponding non-scanning systems, as it also has to capture the footprint of the moving beam.

An analogous example is that of a periscope of the type used in a submarine or as used in ground-based military operations in which the observer's eye(s) are located a good distance from the other end of the periscope and the observer is essentially looking through a long tube in which the view will be very narrow.

If the size of the delivery mirror is increased, it begins to encroach on, and in addition partially obscure the binocular field of view in the observation device.

The disadvantages and technical problem with this design in systems known in the industry, where scanning of the target tissue is effected by scanning the laser beam across the delivery mirror, will be immediately apparent to one of ordinary skill in the art.

In the surgical laser treatment industry, the market wishes for an ideal 50 micron maximum spot size of the laser beam on the target tissue in non-scanning systems. In scanning systems known in the industry, the spot diameter of the laser beam is typically limited to 100 micron or larger, which is too big for many clinical applications, in particular for ophthalmic retinal procedures.

Again, the disadvantages and technical problem with this design in systems known in the industry, where scanning of the target tissue is effected by scanning the laser beam across the delivery mirror, will be immediately obvious to one of ordinary skill in the art.

There is a need for scanning systems in clinical applications, in particular in areas to which access is hampered or confined, such as in ophthalmic retinal procedures, to have the capability of aiming at and treatment of target tissue with a laser beam. However, each such function needs laser beams of different wavelengths and intensities to be scanned across the area to be treated at different velocities and in different modes, and to be activated in different patterns and in different modes. This means that the pair of scanning mirrors that direct the laser beams must have the capability of moving the beams at different velocities and in different modes, and in different patterns, as necessitated by the different functions of the beams.

For example, scanning of target tissue calls for the aiming beam to be scanned rapidly across the area to be treated in a desired two-dimensional pattern across the area to be treated. Hence the pair of scanning mirrors needs to be independently controlled to be moved quickly in such a manner as to scan and generate the desired pattern on the treatment area. The aiming laser beam is typically lower in power density as compared to the treatment laser beam.

In contrast, the latter demands a different movement of the treatment laser beam between spots on the treatment area in a desired pattern, positioning the spot of the activated laser beam on these points without moving for a relatively long desired dwell time sufficient to achieve the desired effect in the target tissue At the beginning of the dwell time, the treatment laser beam is activated and held on a point on the treatment area for the dwell time, at the end of which the treatment laser beam is deactivated and moved to the next point on the treatment area, where the procedure is repeated. The dwell time, at the beginning of which the treatment laser beam is activated, is long enough in order to deliver enough energy and to create the desired tissue effect, for example photo-coagulation.

Then either the inactivated beam is moved at a slower speed than for the aiming beam (as there is no absolute need for speed) to the next spot, or preferably moving the still-activated beam very rapidly to the next treatment spot in a time short enough to avoid treatment taking place on the intervening tissue. (The treatment laser beam is typically higher in power density as compared to the aiming laser beam.)

As noted above, each of the pair of scanning mirrors and the treatment laser beam thus needs to be independently controlled to be moved and activated in such a manner as to generate not only this laser pattern and timing on the treatment area, but also the very different velocities, modes and patterns necessitated by the different function of the scanning laser beam as compared to the treatment laser beam, and to be able to change rapidly between them.

There is thus a call for a drive means for the pair of scanning mirrors that can not only operate faster, but with high controllability and in a synchronized manner at all the different velocities, modes and patterns necessitated by the different system capabilities, for a high quality, precise optical control means for the pair of scanning mirrors and the laser device, which is easily controlled, and for a system with improved safety, in particular in areas to which access is hampered or confined, such as in ophthalmic retinal procedures.

Improved safety, in particular in areas to which access is hampered or confined, especially in ophthalmic retinal procedures also demands that any control means for the pair of scanning mirrors and the laser device should comprise an automatic lock on the treatment laser source which prevents the source being activated and projected onto the retina via the delivery mirror while the scanning mirrors are still directing the optical axis of the system downstream of the delivery mirror onto the fovea or any other aiming point outside the treatment area.

We have now devised an easily controllable system for binocular observation, scanning and treating target tissue by projecting a laser beam onto it, of improved safety, in particular in areas to which access is hampered or confined, such as in ophthalmic retinal procedures, which provides a solution to the disadvantages and technical problem of the design of systems known in the industry.

SUMMARY OF THE INVENTION

Thus, in accordance with a first aspect, the present invention provides a device for scanning and treating target tissue respectively by projecting an aiming laser beam and treatment laser beam onto and across the tissue comprising an aiming laser source and a treatment laser source; at least a pair of scanning mirrors on which a laser beam is incident in use, which are independently controllable to be moved in use to any desired positions and in any desired pattern defined by multiple positions of the scanning mirror positions, and which in use reflect the laser beam into a field lens system; and a delivery mirror for delivering a laser beam from the lens system onto the target tissue, characterised in that the lens system forms a static pupil on the delivery mirror which is independent of any movement, position or pattern defined by multiple positions of the scanning mirrors.

A second aspect of the present invention provides a system for binocular observation of, and scanning and treating target tissue by projecting an aiming and a treatment laser beam onto and across the tissue comprising a device for scanning and treating target tissue of the first aspect of the present invention; linked to a binocular observation device, such that the mirror is located between the longitudinal axes of the two components of the binoculars, and deflects the scanning and treatment beams to be coincident with the central optical axis of the binoculars.

In such a system for binocular observation of, and scanning and treating target tissue, the aiming laser beam or treatment laser beam is often projected onto the area of target tissue to be treated in a direction orthogonal to its direction upstream of the mirror.

The field lens system forms a static pupil. A static pupil is one which forms on the delivery mirror but which is independent of any movement, position or pattern defined by multiple positions of the scanning mirrors, rather than scanning of the target tissue being effected by scanning the laser beam across the delivery mirror.

It will be clear to one of ordinary skill in the art that because, the linkage between the size of the delivery mirror and the scanned treatment area is avoided, thus solving the disadvantages and technical problem with that design in systems known in the industry.

It will also be evident to one of ordinary skill in the art that because the lens system forms a static pupil on the delivery mirror which is independent of any scanning mirror movement, and the size of the scanned treatment area is independent of the size of the delivery mirror, then in order to increase the treatment area a bigger delivery mirror is not required, thus avoiding the technical problem of the delivery mirror encroaching on the binocular field of view in the observation device.

Conversely, in the system of the present invention, for any given size of the treatment area that of the delivery mirror may be decreased, such that it may readily fit is the limited space between the two components of the binoculars.

The only other limitation on the minimum area of the delivery mirror located between the two components of the binoculars is the spot size of the relevant laser beam at this point, which is largely determined by the core diameter and the numerical aperture (NA) of the laser beam delivery fibre. A typical delivery fibre for ophthalmic laser systems has a 50 μm diameter core with a 0.12 NA. The smallest spot size desired by the ophthalmic treatment laser market is 50 μm, but the necessary NA of the laser delivery system is between 0.06 and 0.09 depending on the slit lamp used. A desired size of the delivery mirror may be achieved by providing a desirable spot size by aperturing the beam at an image plane of the output of a typical core fibre, as described in more detail hereinafter.

The laser scanning and treatment device of the first aspect of the present invention may be a stand-alone scanner, which may be linked to a binocular observation device for observing an area of the tissue to be treated, in particular where binocular observation of target tissue during scanning and treating is carried out with a slit lamp of a conventional design, as known in the art.

Another approach is have the scanner device of the first aspect of the present invention integrated into a system of the second aspect of the present invention, in general in particular in areas to which access is hampered or confined, such as in ophthalmic retinal procedures, and where binocular observation of target tissue during scanning and treating is carried out with a slit lamp of a conventional design, as known in the art.

Both the stand-alone scanner device which may be linked to a binocular observation device and the system into which the scanner is integrated provide a solution to the disadvantages and technical problems of known systems, where there is a linkage between the size of the scanned treatment area and the size of the delivery mirror.

In the stand-alone scanner device, the laser sources, scanning mirrors, lens system, delivery mirror and control mechanisms for the laser sources and scanning mirrors are all mounted in a single body.

In the binocular observation device, the binoculars, light for binocular observation of target tissue (often a slit lamp), and safety coatings and mechanisms to protect the operator's eyes from back-scattered energy are all mounted in a single body.

In the system in which the scanning and treatment device and the binocular observation device, are integrated, all the components of the laser scanner device, including the laser sources, scanning mirrors, lens system, and delivery mirror, and of the binocular observation device, the binoculars, light for binocular observation of target tissue (often a slit lamp), and safety coatings and mechanisms to protect the operator's eyes from back-scattered energy are all mounted in a single body.

In the laser device of the first aspect of the present invention, and in the system of the second aspect of the present invention, in particular when used in areas to which access is hampered or confined, such as in ophthalmic retinal procedures, suitable laser beam operating parameters for the scanning, aiming and treatment lasers, such as a wavelengths and power density, may include the following:

The aiming laser beam may suitably produce the desired beam with a lower power density as compared to the treatment laser beam, as a continuous wave or pulsed laser beam having a wavelength in the range of about 500 to 700 nm, for example 625 to 675 nm, such as a solid-state diode laser which provides a 635 nm red beam. The aiming laser beam may be used to draw various patterns of planned treatment spots on the target tissue to show the physician where to operate, and in for example ophthalmic retinal surgical laser treatment, to fixate the patient's eye, the device needs to be capable of being modulated very rapidly to support these applications.

This aiming beam may suitably operate at an average continuous wave output power of no more than 1 mWatt, and in pulsed mode it can be modulated to pulse widths of about 10 microseconds with peak powers of no more than 1 mWatt.

The laser for treating target tissue may suitably be higher in power density than the aiming laser, often as a pulsed or continuous wave laser beam having a wavelength in the range of about 400 nm to 1,200 nm, for example 500 to 1,100 nm.

Depending on the particular ophthalmic treatment mode, the treatment laser may for example be: a pulsed Q-switched Nd:YAG laser with a wavelength of 1064 nm, at 0.3 to 10 mJ per pulse, with a pulse duration of 3 ns, and in burst mode at selectable 1 to 3 pulses per burst, and a repetition rate of 3 Hz; a pulsed Q-switched frequency-doubled Nd:YAG laser with a wavelength of 532 nm, at 0.3 to 2 mJ per pulse, with a pulse duration of 3 ns, and a repetition rate of 3 Hz; a pulsed diode-pumped solid state laser with a wavelength of 532 nm, at 50 mW to 2.5 W, with a pulse duration of 0.001 to 3 s.

FIGS. 1 to 7 of the drawings depict various embodiments of the present invention for purposed of illustration only of the principles of the inventions described herein.

DETAILED DESCRIPTION OF THE PREFERRED EMBODIMENTS

Depending on the type of tissue and the intended tissue effect, other treatment lasers suitable for other treatments will be known to one of ordinary skill in the art.

Figure 5:
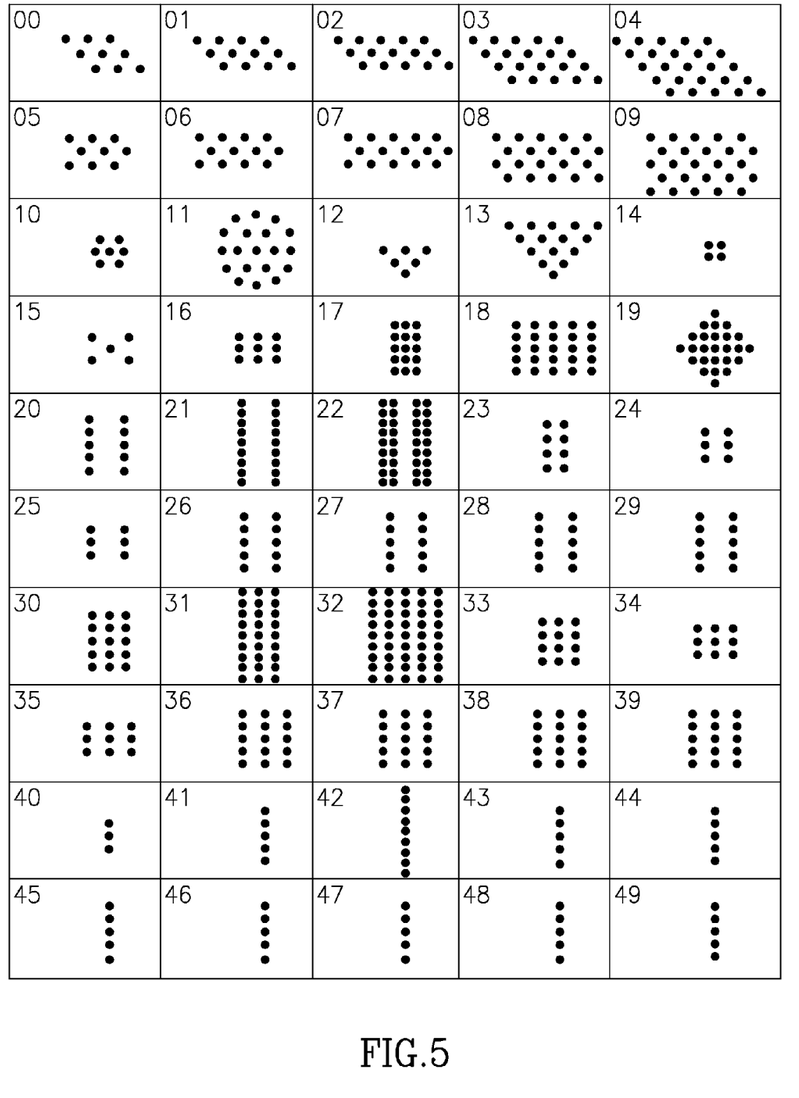
FIG. 5 illustrates a number of laser treatment patterns which may be created with the systems of FIGS. 1 to 4.

The beam of either of the lasers may initially be a collimated or divergent laser beam. In the latter case it may suitably be incident in use on lenses which make the laser beam convergent to form a pupil on the at least a pair of scanning mirrors, which are independently controllable to be moved in use to any desired positions and in any desired pattern defined by multiple positions of the scanning mirror positions (as shown in FIG. 5).

In one embodiment of the laser device, the laser device has a single pair of scanning mirrors on which a laser beam is incident in use.

The pair of scanning mirrors is conveniently of a conventional design, as described in the definition of the scanning mirrors at the beginning of this specification. The rotary galvanometers which are drive means for the pair of scanning mirrors about their pivot axes of rotation of the mirrors should be able to operate with high controllability at all the different velocities, modes and patterns needed.

In ophthalmic retinal procedures in particular, while marking the planned treatment spots with the aiming beam and also drawing laser working parameters on the periphery of the physician field of view, there is a need at the same time to fixate patient's eye with some pattern to capture his attention in his field of view, and much faster scanning rates than in pure treatment are required. In such procedures, the galvanometers should preferably be powered and controlled so as to have the capability to drive the pair of scanning mirrors to scan faster than in conventional scanner designs.

In particular, in ophthalmic laser procedures, it is desirable to mark the planned treatment spots with an aiming beam, while at the same time to fixate patient's eye with some pattern to capture his attention in his field of view and also for example drawing laser working parameters on the periphery of the physician's field of view, which requires much faster scanning then in the case of the scanning of known treatment beams.

Ways in which this may be achieved will be apparent to, or may be found without undue experimentation by, one of ordinary skill in the art.

The pair of scanning mirrors should have the capability to work at an incident treatment laser beam of up to 2.5 Watt without any thermal problems. The mirrors should be made of a material appropriate to the operating parameters of the aiming and treatment lasers in the device, which will be a conventional material known in the art.

In use, the laser beam output from the scanning mirrors is convergent and generally orthogonal to its direction upstream of the mirrors (as shown in FIGS. 1 to 4).

It passes through a first array of two field lenses downstream of the two scanning mirrors. A major role of this array is to perform an astigmatic relay of a static pupil eventually onto the deliver mirror.

The first lens is often an achromatic doublet of a conventional design known in the art, and the second is often a cylindrical field lens that compensates for the small astigmatic deviation from the ideal axial symmetry of the scanning laser beam caused by the small clearance between the two mirrors which allows them to move independently without fouling each other. The compensating parameter is the radius of curvature of the cylindrical field lens. The field lenses are positioned along the optical path of the beam. In order to generate the static pupil on the delivery mirror which is independent of any movement, position or pattern defined by multiple positions of the scanning mirrors, the lenses must be on the image plane of the scanning mirrors.

As such, in order not to distort the image they must be of high quality, and should be made of materials appropriate to the operating parameters of the aiming and treatment lasers in the device, which will be conventional materials known in the art.

The design of the optics necessary to produce the desired beam characteristics will vary depending on the configuration of the optical elements used and the characteristics of the lenses. Ways in which this may be achieved will be clear to, or may be found without undue experimentation by, one of ordinary skill in the art.

The output laser beam from the array of two field lenses downstream of the two scanning mirrors then passes through a second array of lenses further downstream (as shown in FIGS. 1 to 4), adjusted such that the output beam from them is convergent as a pupil on a planar delivery mirror, which deflects the beam, generally orthogonally to its direction upstream of the mirror (as also shown in FIGS. 1 to 4) to be coincident with the central optical axis of the binoculars towards the tissue (for example, a retina) on which the binoculars and the laser beam are targeted, and hence to locations on the target tissue as an image plane.

It will be plain to one of ordinary skill in the art that in the pupil on the planar delivery mirror, the laser beam hits the same spot on the delivery mirror and the beam is not moving. The pupil serves as a pivot point for the beam reflected from the pupil on the delivery mirror (as shown by comparing FIGS. 1 and 2 or 3 and 4).

It will also be understood by one of ordinary skill in the art that, unlike corresponding scanner devices of conventional design, as known in the art, and systems into which such a scanners is integrated with a binocular observation device, there is no linkage between the size of the scanned treatment area and the size of the delivery mirror in the scanner device of the first aspect of the present invention or the system of the second aspect of the present invention. This provides a solution to the disadvantages of such scanning and treating devices and systems, in particular when used in areas to which access is hampered or confined, such as in ophthalmic retinal procedures.

As noted above, the delivery mirror in such a system with a scanning laser beam device linked to, or integrated with, a binocular observation device is often located between the longitudinal axes of the two components of the binoculars, and deflects the scanning and treatment beams to be coincident with the central optical axis of the binoculars. This location constrains the size of the delivery mirror, and drives the need for a static pupil, although other locations of the delivery mirror, such as above, below or on either side of the binocular axis are within the scope of the present invention. The delivery mirror located between the two components of the binoculars is commonly a disc of round, preferably circular cross-section.

In such a system, for any given size of the treatment area that of the delivery mirror may be decreased, such that it may readily fit is the limited space between the two components of the binoculars, which will vary with and will need to be adapted to each different type of binocular system to which the scanning device is linked or into which it is integrated.

The maximum size of the delivery mirror as above will be determined by the limited space between the two components of the binoculars. For a typical binocular device, a typical delivery mirror can deliver a scanning area on the target tissue that is significantly larger than that provided by scanning systems known in the industry), of the order of, for example 30 to 50 $mm^{-2}$, or a circular area of, for example 6 to 8 mm across. This is in excess of that required by many scanning laser beam clinical applications in which access is hampered or confined, such as in ophthalmic retinal procedures.

For example, the present invention allows scanning a third or more of the adult retina and to project data, such as laser working parameters on the periphery of the operator's field of view. Any known system which scans over the delivery mirror will be able to scan only smaller area on the retina and will not allow the projection of data on side areas around the retina within the operator's field of view.

The delivery mirror should have the capability to work at an incident treatment laser beam of up to 2.5 Watt without any thermal problems. The mirror should be made of a material appropriate to the operating parameters of the aiming and treatment lasers in the device, which will be a conventional material known in the art.

The output scanning laser beam from the first array of two field lenses downstream of the two scanning mirrors may pass directly to the second array of lenses further downstream.

However, a disadvantage of such a configuration of the optical elements is the resultant long linear optical path between the scanning mirrors and the delivery mirror, which in turn results in an inconvenient design of the body of the laser device or the system, which will tend to take up too much space in the treatment room.

Accordingly, the divergent scanning laser beam from the first array of lenses may suitably be incident on a planar fold-in mirror, which deflects the beam, generally orthogonally to its direction upstream of the mirror (as shown in FIGS. 1 to 4) to be incident on the second array of lenses downstream of the fold-in mirror.

This results in a non-linear optical path between the scanning mirrors and the delivery mirror, which in turn results in a more convenient design of the body of the laser device or the system.

The fold-in mirror should have the capability to work at an incident treatment laser beam of up to 2.5 Watt without any thermal problems. The mirror should be made of a material appropriate to the operating parameters of the scanning, aiming and treatment lasers in the device, and have a coated surface of the appropriate quality and for the required angles of incidence, all of which will be conventional materials known in the art.

As noted above, in the surgical laser treatment industry, the market demands a 'gold standard' laser treatment spot diameter of about 50 micron maximum on the target tissue in non-scanning systems. In scanning systems known in the industry, the spot diameter of the laser beam is typically limited to 100 micron or larger, which is too big for many clinical applications, in particular for ophthalmic retinal procedures. Lower diameters, which might be appropriate, have concomitant problems with output power and its temporal stability.

Again, the disadvantages and technical problem with the design of such scanning systems are overcome in one embodiment each of the scanning laser beam device of the first aspect of the present invention and the system of the second aspect of the present invention. Each such embodiment can provide enough optical power to reduce the spot size to 25 to 35 microns, that is, the present invention with a scanning system provides a spot diameter of the laser beam on the target tissue of two thirds to a half of that achievable in non-scanning systems, and a third to a quarter of the spot diameter of the laser beam in scanning systems known in the industry.

Thus, in a preferred embodiment of the laser device of the first aspect of the present invention, the laser device has a single aperture with a diameter which determines the desired spot diameter of the laser beam on the target tissue, in the optical path and at an image plane of the beam, often between the laser source and the at least a pair of scanning mirrors on which a laser beam is incident in use, preferably between the laser source and the first array of lenses before the mirrors.

The diameter of the aperture is not necessarily that of the desired spot diameter of the laser beam on the target tissue, but the correlation between the spot diameter and the aperture diameter will be known to one of ordinary skill in the industry, or may be readily determined found undue experimentation by, one of ordinary skill in the art.

In theory, the diameter of the aperture may be reduced to the diffraction limit with respect to the wavelength of the beam that passes through the aperture. For the typical wavelengths for ophthalmic retinal procedures, given hereinbefore, the corresponding diameter of the aperture is of the order about 10 micron. The smallest diameter of the laser beam spot (25 to 35 micron) corresponds to an aperture diameter of this order. The aperture diameter is in any event smaller than the diameter of the laser beam at the point where it strikes the aperture.

The aperture often passes orthogonally through a plate itself mounted orthogonally to the optical path of the laser beam.

The plate thickness should be greater than the depth of focus of the image at the aperture plane, and is commonly in a range of about 100 to 500 micron, with an aperture diameter of the order of about 10 micron.

The plate should be made of a material appropriate to the operating parameters of the aiming and treatment lasers in the device, such as a metal, preferably a corrosion resistant metal and in particular titanium or a titanium steel. The plate generally has a refractory coating, to reduce its deterioration in the incident laser beams in use.

The aperture may in general be a hole of round, preferably circular cross-section, which may be drilled by laser or water jet through the plate thickness.

Although placing the aperture on an image plane causes energy loss in the incident laser beam, in particular in the treatment beam spot (preferably of 25 to 35 micron diameter) most suited to ophthalmic retinal procedures, the resultant energy loss is predictable and can be compensated, for example by increasing the energy density of the incident laser in a conventional manner known in the art.

Similarly, in a preferred embodiment of the system of the second aspect of the present invention, the system has a single aperture with a diameter which corresponds to the desired spot diameter of the laser beam on the target tissue, in the optical path of the beam between the laser source and the at least a pair of scanning mirrors on which a laser beam is incident in use, preferably close to the laser source.

The preferred embodiment of the system of the second aspect of the present invention will have similar, if not the same, construction and operating parameters as those of the scanning laser device above.

In use of the system of the second aspect of the present invention, the system operates with high controllability in the following modes and patterns. The following description is of such use in ophthalmic retinal procedures, but it may be adapted is scanner to other surgical laser procedures mutatis mutandis in particular for other areas to which access is hampered or confined.

A first mode comprises eye fixation and treatment marking with aiming and scanning laser sources. A second mode is the treatment mode.

In the first mode, the aiming beam (often a red diode laser) aligned with the optical path of the (inactive) treatment laser beam is used to fixate the patient eye by focusing it on the fovea, and the aiming beam "draws" and marks the desired treatment pattern on the target tissue (which is not the fovea but elsewhere on the retina) often with spots in multiple positions on the treatment area of the retina, and may also mark information, such as laser operating parameter information, outside the target tissue towards the periphery of the field of view of the physician. The spots may each independently be of the same of the same diameter as the desired diameter of the treatment laser beam at each spot position.

Scanning is normally effected by moving the scanning mirrors very quickly.

Before the treatment laser is activated to treat the target tissue, the optical axis of the system on the retina is moved away from the fovea and is targeted on the desired treatment area.

The control means for the pair of scanning mirrors and the laser device should comprise an automatic lock on the treatment laser source which prevents the treatment laser source being activated and projected onto the retina via the delivery mirror while the scanning mirrors are still directing the optical axis of the system downstream of the delivery mirror onto the fovea or any other aiming point outside the treatment area. Such a lock is described further below in this specification in relation to the use of a smart switch, conveniently a unidirectional footswitch, which may form part of the control means.

The treatment laser beam is then moved, activated under the control of the lock on the treatment laser source, which prevents the treatment laser beam from being projected via the delivery mirror onto other than the target tissue without the necessary movement occurring, and projected onto the target tissue via the delivery mirror in such a manner as to treat the target tissue in the scanning laser pattern with the necessary dwell time and power density at any treatment spots for the desired treatment. It will be appreciated that this requires successive intermittent slow movement of the scanning mirrors with the desired dwell times.

A third aspect of the present invention thus provides a method of scanning a laser beam onto a target with a device for scanning a target by projecting a scanning laser beam onto and across the target, the device comprising a scanning laser source; at least a pair of scanning mirrors on which a laser beam is incident in use, which are independently controllable to be moved in use to any desired positions and in any desired pattern defined by multiple positions of the scanning mirror positions, and which in use reflect the laser beam into a lens system; and a delivery mirror for delivering a laser beam from the lens system onto the target tissue, the method of scanning a laser beam onto a target comprising activating the scanning laser source; and moving the scanning mirrors in such a manner as to generate a desired laser pattern on the target characterised in that the lens system forms a static pupil on the delivery mirror which is independent of any movement, position or pattern defined by multiple positions of the scanning mirrors.

The scanning laser in this method may be an aiming laser or a treatment laser.

A fourth aspect of the present invention provides a method of surgical laser treatment with a system for scanning and treating target tissue comprising a system for binocular observation of the target tissue; linked to, or integrated with, a device for scanning and treating target tissue, the device comprising an aiming laser source and a treatment laser source; at least a pair of scanning mirrors on which each laser beam is incident in use, which are independently controllable to be moved in use to any desired positions and in any desired pattern defined by multiple positions of the scanning mirror positions, and which in use reflect each laser beam into a lens system; and a delivery mirror for delivering a laser beam from the lens system onto the target tissue, the method of treatment with comprising activating the aiming laser source, and moving the scanning mirrors in such a manner as to generate a desired scanning laser pattern on the target; and then activating the treatment laser source, and moving the scanning mirrors in such a manner as to treat the target tissue in a desired laser pattern on the target characterised in that the lens system forms a static pupil on the delivery mirror which is independent of any movement, position or pattern defined by multiple positions of the scanning mirrors.

As noted above, there is a call for a drive means for the pair of scanning mirrors that can not only operate faster and in a synchronized manner, but with high controllability at all the different velocities, modes and patterns necessitated by the different system capabilities, and to be able to change rapidly between them.

There is also a demand for a high quality, precise optical control means for the pair of scanning mirrors and the laser device, which affords easy independent control of the aiming and treatment laser beams in the method of surgical laser treatment of the fourth aspect of the present invention.

The above treatment regimen may be conveniently implemented using a smart switch, conveniently a unidirectional footswitch, which in all other respects is of a conventional design. The switch is configured such that when an operator actuates it, for example, by depressing a footswitch, it causes the system to move through the modes described in this specification in relation to the use of the system of the second aspect of the present invention. The following description is of such use in ophthalmic retinal procedures, but it may be adapted is scanner to other surgical laser procedures mutatis mutandis, and be modified in details as may be appropriate for any procedure.

Thus initial actuation, for example, by depressing a footswitch, activates the system in the first mode, that is, it activates eye fixation and treatment marking with aiming and scanning laser sources. In more detail, it activates the aiming beam (often a red diode laser) to fixate the patient eye by focusing it on the fovea, and activates and moves the aiming beam in a desired treatment pattern on the target tissue, and marks the treatment positions on the treatment area of the retina and optionally data, such as laser working parameters, on the periphery of the operator's field of view.

The next actuation deactivates the aiming laser source, and moves the optical axis of the system on the retina away from the fovea to target the desired treatment area, and moves and projects the treatment laser beam onto the target tissue via the delivery mirror in such a manner as to treat the target tissue in the aiming laser pattern with the necessary dwell time and power density at any treatment spots for the desired treatment.

As noted above, the control means for the pair of scanning mirrors and the laser device should comprise an automatic lock on the treatment laser source which prevents the source being activated and projected onto the retina via the delivery mirror while the scanning mirrors are still directing the optical axis of the system downstream of the delivery mirror onto the fovea or any other aiming point outside the treatment area.

Such a lock may conveniently be in the form of an automatic override of any signal from a unidirectional footswitch to activate the treatment laser source and projected its beam onto the retina via the delivery mirror while the scanning mirrors are still directing the optical axis of the system downstream of the delivery mirror onto the fovea or any other aiming point outside the treatment area.

The final actuation deactivates the treatment laser source.

The theory of operation of the system of the present invention can be explained by reference to FIGS. 1 and 2.

Figure 1:
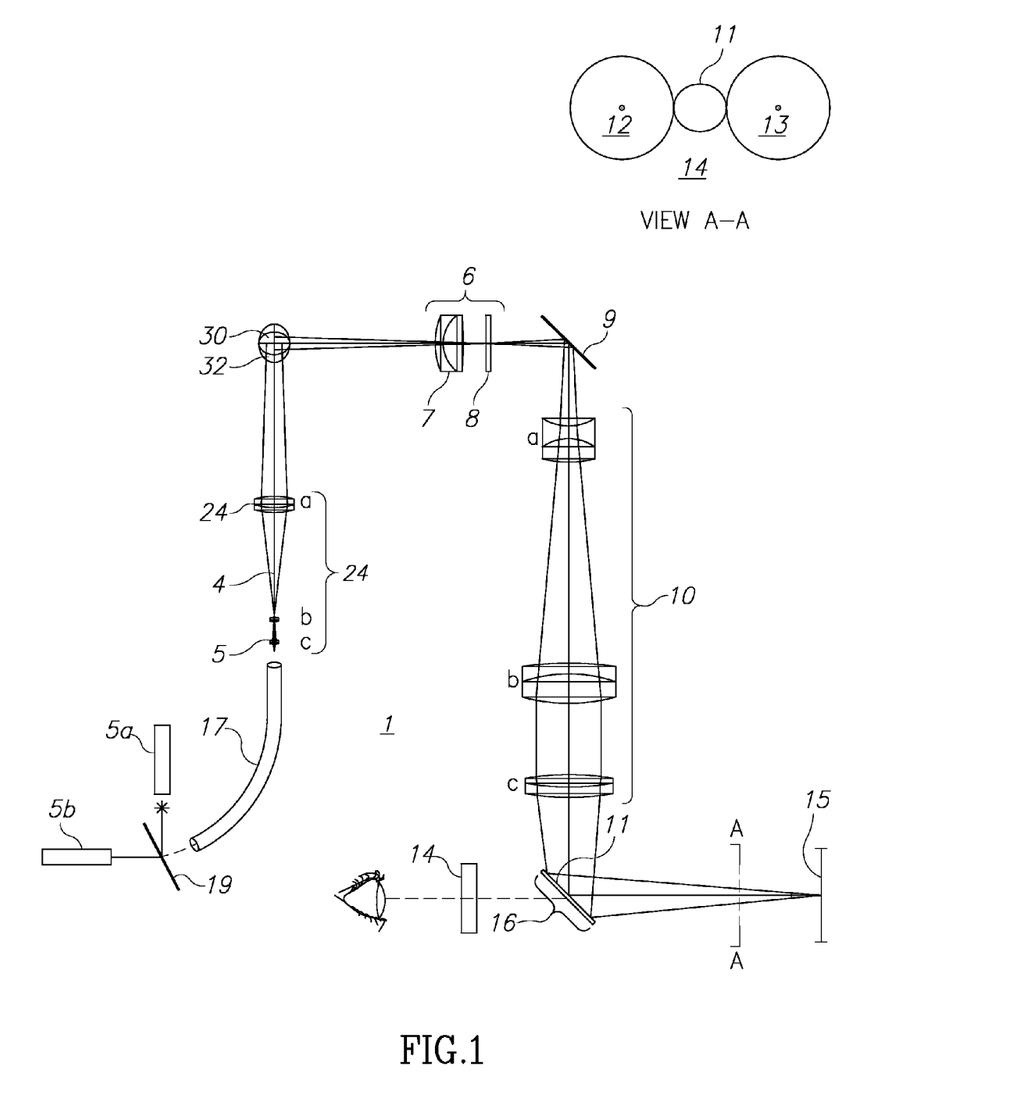
FIG. 1 is a schematic view of one embodiment of a system according to the present invention.

In FIG. 1, the system 1 includes a laser beam 4, which may be an aiming laser beam or a treatment laser beam. The laser beam is sourced from a laser sources 5a and 5b respectively. The laser sources 5a and 5b may impinge on a known combiner mirror or prism arrangement which will allow one or both laser sources to transmit a laser beam to, by way of example, a step-index multi-mode optical fiber 17. The laser beam(s) will then travel through the optical fiber 17 to a lens array 24. The structure and operation of the lens array 24, which in the present embodiment may comprise three lenses 24a, 24b and 24c, will be explained below.

Figure 2:
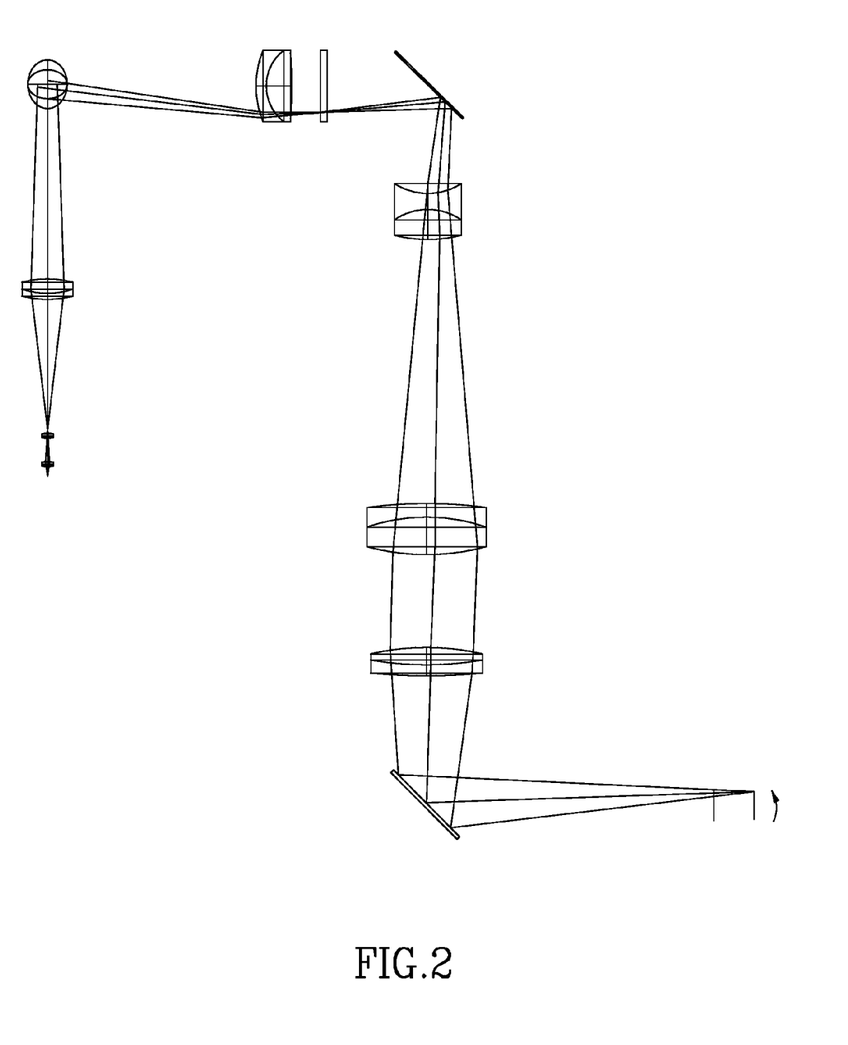
FIG. 2 is a schematic view of the embodiment of FIG. 1.
Figure 6:
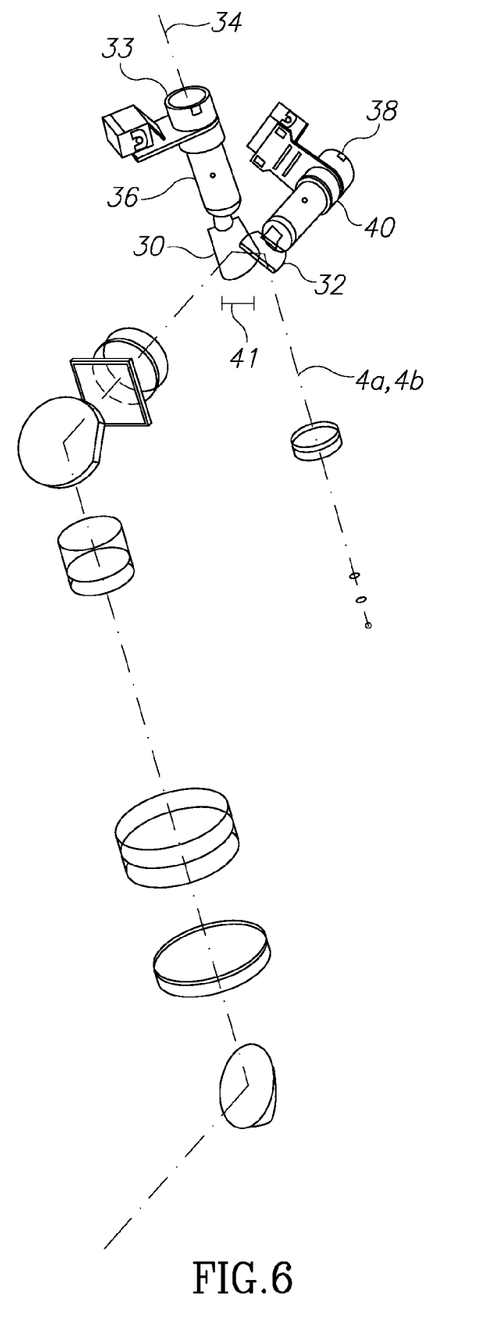
FIG. 6 is a schematic view of an arrangement of scanning mirrors which may be used with the embodiments of FIGS. 1 to 4.

As shown in FIGS. 1 and 2, the laser system 1 has two independently controlled mirrors 30, 32 that scan the laser beam 4 in two orthogonal directions. As illustrated in FIG. 6, mirror 30 is mounted on a mirror mount 33 and is pivoted about axis 34 by a rotary galvanometer 36. Mirror 32 is pivoted about an axis 38 by another rotary galvanometer 40. The axes of rotation of the mirrors 30, 32 are mutually orthogonal and are also orthogonal to the incident laser beam 4. The galvanometers 36, 40 are powered and controlled by a controller (not shown) in a known conventional manner that supplies appropriate voltages to the galvanometers to cause them and the attached mirrors to rotate to the desired positions.

The two mirrors 30, 32 are separated by a small clearance, shown as 41 in FIG. 6, and create an astigmatic pupil in the system 1. Lens arrays 6 and 10 (to be described in detail below) work in concert to relay the astigmatic pupil at mirrors 30 and 32 to a single pupil position at delivery mirror 11.

The beam 4 passes through a first array 6 of two field lenses downstream of the two scanning mirrors 30, 32.

Downstream of the lens array 6, the optical path of the beam 4 is incident at an angle on a fold-in mirror 9. The fold-in mirror 9 deflects the beam 4 generally orthogonally (although other angular relationships maybe used) to its direction upstream of the mirror to be incident on a second array of lenses 10 downstream of the fold-in mirror 9. Passage of the light beam 4 through the second array of lenses 10 downstream of the fold-in mirror 9 transmits the light beam to a delivery mirror 11.

The structure and operation of lens arrays 6, 10 and 24 and their component lenses 7, 8, 10a, 10b, 10c, 24a, 24b and 24c will now be described.

Lenses 24a, 24b, and 24c together comprise a par-focal, variable-magnification microscope that generates a real-image conjugate of the fiber output within lens array 6. Lenses 24a and 24b move axially in position, allowing magnifications at image plane 15 to vary from 1.4× to 20×.

The glass thicknesses, glass types, air spacings, and radii of curvature were simultaneous constraints on lens 7 and the lenses in array 10 in order to create an f-theta image relay system such that the fiber image within lens array 6 is relayed to image plane 15.

The glass thicknesses, glass types, air spacings, and radii of curvature were simultaneous constraints on the lenses in array 6 and the lenses in array 10 in order to create a pupil relay system such that the astigmatic pupil created by mirrors 30 and 32 is relayed to the non-astigmatic pupil 11 at delivery mirror 16.

Lens 7 may be a positive achromatic doublet consisting of a negative effective focal length (EFL) convex-concave element which may be made of S-LAH66 glass cemented to a positive EFL convex-convex element which may be made of S-LAL13. The gross function of lens 7 is to act as a field element to relay the pupil at 30 & 32 to the pupil at 11. Lens 7 also helps lens array 24 to create a sharp image of the fiber within lens array 6.

Lens 8 may be a singlet consisting of a positive EFL plano-cylindrical lens which may be made of N-BK7 glass. The gross function of lens 8 is to correct the astigmatism in the pupil caused by separation 41 between mirrors 30 and 32. Inasmuch as the scratch-dig surface quality of both surfaces of lens 8 is high (10-5 or less), the fiber image in lens array 6 will not be degraded.

Lens 10a may be a negative achromatic doublet consisting of a negative EFL concave-concave element which may be made of S-BSM28 glass cemented to a positive EFL convex-convex element which may be made of S-TIM22 glass. The gross function of lens 10a is to increase the beam divergence and thus shorten the length of the optical system. Lens 10a also helps to generate a sharp image of the fiber at image plane 15 and to relay the pupil from mirrors 30 and 32 to 11.

Lens 10b may be a positive achromatic doublet consisting of a negative EFL convex-concave element which may be made of S-TIH4 glass cemented to a positive EFL convex-convex element which may be made of S-BSM28 glass. The gross function of lens 10b is to collimate the laser beam. Lens 10b also helps to generate a sharp image of the fiber at image plane 15 and to relay the pupil from mirrors 30 and 32 to 11.

Lens 10c may be a positive achromatic doublet consisting of a positive EFL convex-convex element which may be made of N-SK11 glass cemented to a negative EFL concave-convex element which may be made of N-SF5 glass. The gross function of lens 10c is to focus the laser beam as an objective lens to generate a sharp image of the fiber onto image plane 15. Lens 10c also helps to relay the pupil from mirrors 30 and 32 to 11.

Figure 3A:
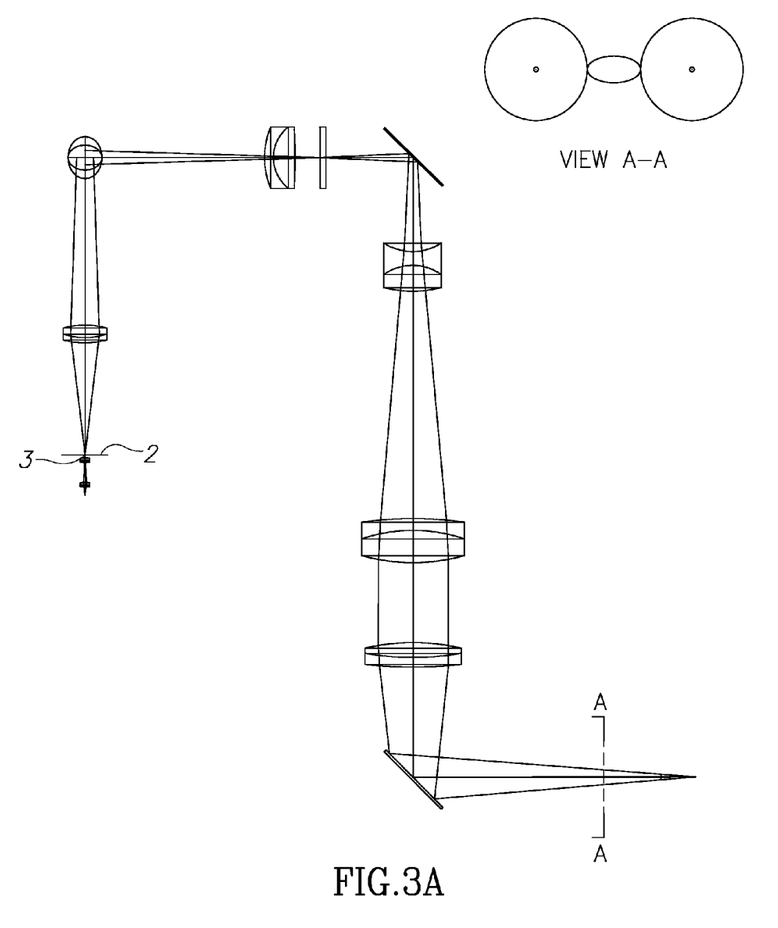
FIGS. 3a and 3b are schematic views of another embodiment of a system according to the present invention.
Figure 7:
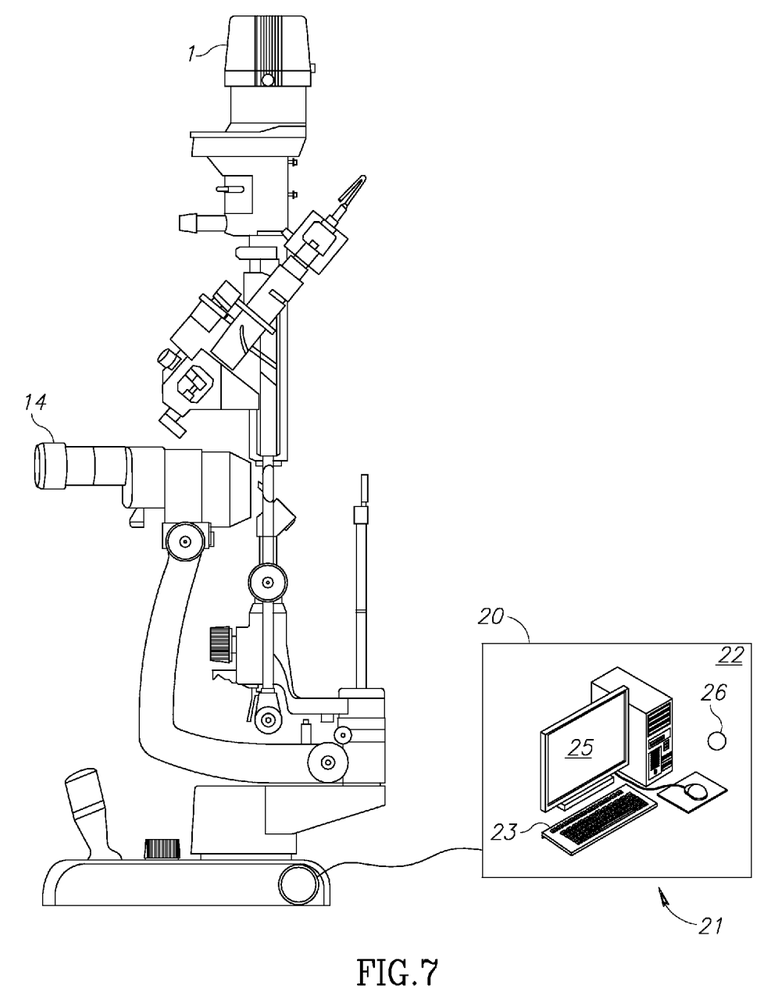
FIG. 7 is a schematic view of a binocular apparatus and control system that may be used with the embodiments of FIGS. 1 to 4.

Returning now to a description of the system 1, the delivery mirror 11 is located between the longitudinal axes 12, 13 of the two components of binoculars 14 in the limited space between the two components of the binoculars, here a disc of circular cross-section, as shown in the view on section AA in FIGS. 1 and 3. The binoculars 14 are in a system for binocular observation of target tissue during scanning and treatment, here a slit lamp. The structure of the binocular components is illustrated in FIG. 7 of the drawing figures. The delivery mirror 11 deflects the beam 4 to be coincident with the central optical axis of the binoculars 14 in a direction orthogonal to its direction upstream of the mirror 11 onto target tissue 15 for scanning and treatment.

The system operator is to the viewer's left of the delivery mirror 11 as shown in by the depiction of an eye in FIG. 1, observing the target tissue 15 for scanning and treatment through the binoculars 14 in the direction of the beam 4 downstream of the mirror 11.

The laser beam 4 incident on the delivery mirror 11 as shown in FIGS. 1 and 2, forms a static pupil 16 on the delivery mirror 11. As may be seen by comparing the laser beam 4 position on the delivery mirror 11 in FIGS. 1 and 2, as well as comparing FIGS. 3 and 4 (further described below), the pupil 16 is static on the delivery mirror 11, independently of any movement, position or pattern defined by multiple positions of the scanning mirrors 30, 32. The pupil serves as a pivot point for the beam reflected from the pupil on the delivery mirror (as shown by comparing FIGS. 1 and 2 and 3 and 4).

It will also be seen that, unlike corresponding systems of conventional design, as known in the art, there is no linkage between the size of the scanned treatment area 15 and the size of the delivery mirror 11 in the device of the first aspect of the present invention or the system of the second aspect of the present invention. This enables the delivery mirror 11 to be located in the limited space between the two components of the binoculars 14. without sacrificing the size of the operator's field of view.

The system 1 shown in FIG. 7 may house all of the components of the system 1 illustrated in FIGS. 1 to 4.

The system 1 may include a programmable control system 20 in operative connection with the system 1. The controller 20 may be used to control the lasers 5a and 5b and the binocular system 14, preferably located conveniently close to the operator viewing through the binoculars 14. The control system 20 is actuated, for example, by depressing a unidirectional footswitch 21.

A control panel 22 is used with the control system 20. The operator may select a numbered pattern by entering one or more entries on a key pad 23. The pattern number may be displayed on a display 25. FIG. 5, by way of example only, illustrates various patterns that may be used with the system 1. The operator can also select on the control panel 22, using a button 26, whether the pattern is to be delivered once or repeatedly, as indicated on the display 25.

In operation, the operator selects a pattern on keypad 23, and single/repeat scanning on button 26 on the control panel 22 of the system 1. Initial actuation, for example, depressing the footswitch 21, may activate the system in a first mode, that is, activating eye fixation and treatment marking with aiming laser source. In more detail, may activate the aiming beam (often a red diode laser) to fixate the patient eye by focusing it on the fovea, and may activate and move it in a desired treatment pattern on the target tissue, and marking the treatment positions on the treatment area of the retina. Instead of a physical keypad, a touchscreen device may be utilized.

The next actuation deactivates the aiming laser source, and moves the optical axis of the system on the retina away from the fovea to target the desired treatment area, and moves and projects the treatment laser beam onto the target tissue via the delivery mirror in such a manner as to treat the target tissue in the marked laser pattern with the necessary dwell time and power density at any treatment spots for the desired treatment.

The final actuation deactivates the treatment laser source 5.

Figure 3B:
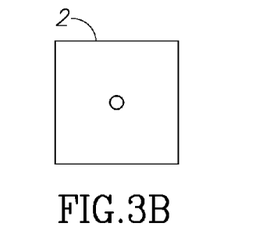

A schematic view of another embodiment of the present invention is shown in FIGS. 3a and 3b, which is identical to the system 1 shown in FIGS. 1 and 2, but with the addition of an apertured plate 2 mounted orthogonally to the optical path of the laser beam 4. It is to understood that FIGS. 1 to 4 encompass the same components (except as described below) but reference numbers for common components have been included only in FIG. 1 for simplicity.

The apertured plate 2 may be made of a reflective metal to reduce its deterioration in the incident laser beam 4 in use.

An aperture 3 of circular cross-section is formed orthogonally through the apertured plate 2 in the optical path of the laser beam 4. The aperture is smaller than the diameter of the laser beam 4 at the point where it strikes the aperture 3.

The apertured plate 2 causes energy loss in the laser beam 4, but the aperture 3 has the capability to produce a treatment beam spot of 50 micron diameter, generally considered to be most suited to ophthalmic retinal procedures, although other diameters may be utilized. The resultant energy loss is predictable and can be compensated in conventional manners known in the art.

Figure 4:
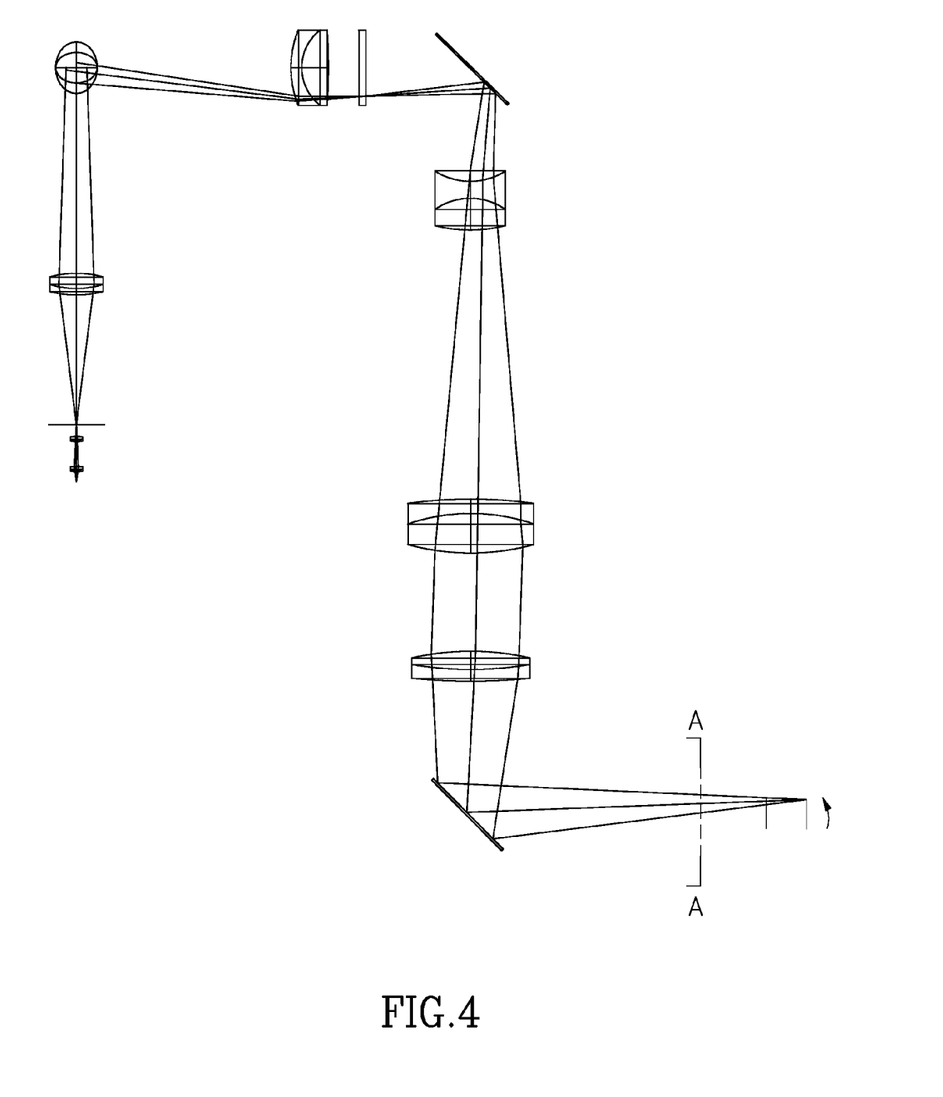
FIG. 4 is another schematic view of the embodiment of FIG. 3.

The operation of the system of FIGS. 3 and 4 is identical to that of the system 1 shown in FIGS. 1 and 2, without any effect of the addition of an apertured plate 2 or the aperture 3, other than the production of a treatment beam spot of 50 micron diameter, and known energy loss in the beam 4, compensated in conventional manners known in the art.

It should be noted that the features and advantages described in the specification are not all-inclusive, and particularly, many additional features and advantages will be apparent to one of ordinary skill in the art in view of the drawings, specification and claims hereof.

It will be apparent that the invention disclosed herein provides a novel and advantageous surgical laser scanner that scans a laser beam onto target tissue. The disclosure of the present invention is intended to be illustrative, but not limiting, of the scope of the invention, which is set forth in the following claims.

What I claim is:

1. A device comprising:
a treatment laser source;
pair of 2 scanning mirrors downstream in an optical path of a laser beam from the treatment laser source, the pair of scanning mirrors being independently controllable to be moved to multiple positions defined by scanning mirror positions; the pair of 2 scanning mirrors producing an astigmatic pupil from a laser beam of the treatment laser source
a first lens system downstream from and in the optical path of a laser beam from the pair of scanning mirrors, the lens system comprising one or more lenses;
further comprising a second lens system in the optical path and downstream of the first lens system, the second lens system adjusting the light beam from the first lens system such that a light beam from the second lens system converges as a pupil on a delivery mirror;
the first lens system and the second lens system together converting the astigmatic pupil to a non-astigmatic pupil;
the delivery mirror being positioned downstream in the optical path of the second lens system, the delivery mirror delivering a laser beam from the first and second lens systems onto the target tissue;
wherein the lens system forms a static pupil on the delivery mirror which is independent of any movement, position or pattern defined by the multiple positions of the pair of 2 scanning mirrors.

2. The device of claim 1, further comprising:
a binocular observation device having a central optical axis and two longitudinal axes operatively associated with the central axis;
the delivery mirror being located between the longitudinal axes of the binocular observation device, and wherein the delivery mirror deflects the laser beam from the treatment laser source to be coincident with the central optical axis of the binocular observation device.

3. The device according to claim 2 wherein the laser beam from the treatment laser source is deflected onto the area of target tissue to be treated in a direction orthogonal to its direction upstream of the mirror.

4. The device according to claim 2, wherein the device is a stand-alone scanner which is linked to a binocular observation device for observing an area of the tissue to be treated.

5. The system according to claim 4 where binocular observation of target tissue during scanning and treating is carried out with a slit lamp.

6. The device according to claim 1 wherein the size of the area of treatment is independent of the size of the delivery mirror.

7. The device according to claim 1, wherein the aiming laser source produces a continuous wave laser beam having a wavelength in the range of about 500 to 700 nm.

8. The device of claim 1, further comprising an aiming laser device positioned in the same optical path of the treatment laser source.

9. The device according to claim 1, wherein the treatment laser source produces a pulsed or continuous wave laser beam having a wavelength in the range of about 500 to 1,100 nm.

10. The device according to claim 9, wherein the treatment laser is one of:
- a pulsed Q-switched Nd:YAG laser with a wavelength of 1064 nm, at 0.3 to 10 mJ per pulse, with a pulse duration of 3 ns, and in burst mode at selectable 1 to 3 pulses per burst, and a repetition rate of 3 Hz; or
- a pulsed Q-switched frequency-doubled Nd:YAG laser with a wavelength of 532 nm, at 0.3 to 2 mJ per pulse, with a pulse duration of 3 ns, and a repetition rate of 3 Hz; or
- a pulsed diode-pumped solid state laser with a wavelength of 532 nm, at 50 mW to 2.5 W, with a pulse duration of 0.001 to 3 s.

11. The device of claim 1, further comprising an aperture positioned between the laser sources and the at least a pair of scanning mirrors for controlling the size of the laser beams from the laser source.

12. The device of claim 11 wherein the aperture comprises a metal plate with an aperture formed therein.

13. The device according to claim 8, wherein the aiming laser source is a solid-state laser diode which produces a continuous wave laser beam having a wavelength of 635 nm.

14. The device of claim 1, wherein the first lens system comprises one or more field lenses.

15. The device of claim 14, wherein the one or more field lenses in the first lens system are positioned on the image plane of the at least one pair of scanning mirrors.

16. The device of claim 14, wherein one of the one or more field lenses in the first lens system is an achromatic doublet having a negative effective focal length (EFL) convex-concave element cemented to a positive EFL convex-convex element.

17. The device of claim 16, wherein another one of the one or more field lenses is a positive EFL plano-cylindrical lens that compensates for the astigmatic pupil from the at least pair of scanning mirrors.

18. The device of claim 1, wherein the second lens system comprises a plurality of lenses to relay the pupil from the scanning mirrors to the delivery mirror.

19. The device of claim 18, wherein one of the lenses in the second lens system is a negative achromatic doublet having a negative EFL concave-concave element cemented to a positive EFL convex-convex element.

20. The device of claim 19, wherein one of the lenses in the second lens system is a positive achromatic doublet having a negative EFL convex-concave element cemented to a positive EFL convex-convex element.

21. The device of claim 20, wherein one of the lenses in the second lens system is a positive achromatic doublet including a positive EFL convex-convex element cemented to a negative EFL concave-convex element.

22. The device of claim 1, further comprising a third lens system positioned downstream of the treatment laser source but upstream of the at least a pair of scanning mirrors, the third lens system comprising a par-focal, variable-magnification microscope which generates a real-image conjugate of the laser output within the first lens system.

23. The device of claim 22, wherein the third lens system variably magnifies at the image plane from 1.4× to 20×.

24. The device of claim 1, wherein the first and second lens systems create an f-theta image relay system such that a laser fiber image within the first lens system is relayed to an image plane of the target tissue.

25. A method of scanning a laser beam onto a target with a device comprising:
providing the device of claim 1;
scanning a treatment laser beam onto a target including activating the scanning laser source;
moving the scanning mirrors to generate a desired scanning laser pattern on the target; and,
wherein the first and the second lens systems form lens system forms a static pupil on the delivery mirror which is independent of any movement, position or pattern defined by multiple positions of the scanning mirrors.

26. A method of surgical laser treatment with a system comprising:
providing the system for binocular observation of the target tissue operatively linked to a device for scanning and treating target tissue of claim 2;
providing an aiming laser device in the same optical path as the treatment laser source;
the method comprising:
activating the aiming laser source;
moving the scanning mirrors to generate a desired scanned laser pattern on the target;
activating the treatment laser source; and,
moving the scanning mirrors in such a manner as to treat the target tissue in a desired laser pattern on the target with the treatment laser source.

* * * * *